United States Patent [19]

Meyer et al.

[11] Patent Number: 4,467,077
[45] Date of Patent: Aug. 21, 1984

[54] MICA FILLED POLYOLEFIN RESIN COMPOSITES

[75] Inventors: Fred J. Meyer, Chelsea; Seymour Newman, Southfield, both of Mich.

[73] Assignee: Ford Motor Company, Dearborn, Mich.

[21] Appl. No.: 239,229

[22] Filed: Mar. 2, 1981

Related U.S. Application Data

[63] Continuation of Ser. No. 970,822, Dec. 18, 1978, abandoned, which is a continuation-in-part of Ser. No. 849,287, Nov. 7, 1977, abandoned, which is a continuation-in-part of Ser. No. 783,505, Mar. 31, 1977, abandoned.

[51] Int. Cl.$^3$ ............................ C08K 3/34; C08K 5/02
[52] U.S. Cl. ..................................... 524/449; 524/465; 524/472
[58] Field of Search ........................ 524/449, 472, 465

[56] References Cited

U.S. PATENT DOCUMENTS 4,001,174  1/1977  Yagi et al. ........................ 204/159.2
4,328,146  5/1982  Andy ................................... 524/472

FOREIGN PATENT DOCUMENTS 1340417  12/1973  United Kingdom .

Primary Examiner—James H. Derrington
Attorney, Agent, or Firm—Peter D. McDermott; Roger L. May

[57] ABSTRACT

Mica filled polyolefin resin composites exhibit improved mechanical properties if the mica filler and polyolefin resin are specially combined with additives comprising chlorinated aliphatic compounds. The composites are preferably made from blends comprising about 1–36 parts by weight mica flakes (especially phlogopite mica), 9 parts by weight propylene resin and minor effective amounts of the additive. Various processing techniques such as selecting the time the blends reside at melt temperatures during compounding permits development of advantageous properties.

38 Claims, No Drawings

MICA FILLED POLYOLEFIN RESIN COMPOSITES

CROSS-REFERENCE TO RELATED APPLICATION

This application is a continuation of U.S. Ser. No. 970,822, filed Dec. 18, 1978, now abandoned, which is a continuation-in-part of U.S. Ser. No. 849,287, filed Nov. 7, 1977, now abandoned, which is a continuation-in-part of U.S. Ser. No. 783,505, filed Mar. 31, 1977, now abandoned.

This application is related to U.S. Ser. No. 849,288, filed Nov. 7, 1977, now abandoned, which is a continuation-in-part of U.S. Ser. No. 783,505, filed Mar. 31, 1977, now abandoned.

U.S. Ser. No. 849,288 relates to silicate fillers and additives as in this application.

Concurrently filed and commonly assigned U.S. Ser. No. 970,838, filed Dec. 18, 1978, now abandoned, entitled "Compounding Mica and Melt Forming Resins with Heat-Sensitive Additives" in name of A. Keeney provides a means for rapid compounding of melt forming resins with mica utilizing certain chlorinated aliphatic compounds as coupling agents and is considered as a disclosure of a current preferred commercial embodiment that is incorporated herein by reference.

Concurrently filed and commonly assigned U.S. Ser. No. 970,821, filed Dec. 18, 1979, now abandoned, by L. Bartosiewicz, entitled "Coated Mica" relates to a desirable means for providing a coating on mica particles that can thereafter be used, for example, in compounding with melt forming resins as herein and such disclosure relating to coating of mica is incorporated herein by reference.

This invention relates to silicate filled resin composites made with additives which comprise chlorinated aliphatic compounds. Inclusion of these additives can enhance mechanical properties of the composites.

Coupling additives for certain inorganic filled resin composites are known. For example, silane compounds are employed in various glass and mica filled resin composites for improving resin reinforcement. Moreover, certain chlorinated aliphatic compounds have been utilized in systems to provide fire retardancy.

It has been now discovered that certain chlorinated aliphatic compounds act to improve mica and polyolefin resin adhesion especially when select melt times and temperatures are used during processing.

Briefly, this invention concerns composites made by a process which comprises combining mica, polyolefin resin, and a minor amount by weight of an additive which comprises one or more chlorinated aliphatic compounds in a way that strengthens the composite. This strengthening is preferably accomplished by selecting the time the blends are exposed to processing temperatures. This strengthening can also be accomplished by exposing the blends to higher temperatures for shorter times. A level of 1-36 parts by weight mica filler for each 9 parts by weight polyolefin resin provides composites of particularly useful properties, whereas a weight ratio of the mica to resin of about 2:5-5:2 (particularly mica at about 30-50% by weight of the composite) normally provides an optimum balance.

Polyolefin resins suitable for this invention include well known, commercially available materials designed for use in molding (as by injection, compression, etc.) and other melt forming processes (as extrusion, stamping, etc.). Of these commercial resins, those made from monomers comprising olefinic hydrocarbons such as ethylene, propylene and butene-1 can provide composites with excellent properties as well as economic advantage. Particularly suitable in this regard are resins comprising polyethylene or polypropylene or copolymers of ethylene and/or propylene as well as blends of any of these. As used herein polyolefin resins means any of the above identified resins that are typically melt formed and are made from monomers comprising olefinic monomers, particularly monomers that are aliphatic hydrocarbon monomers and preferably predominantly by weight 1-olefin hydrocarbons such as ethylene, propylene, butene-1, and 4-methylpentene-1. Such polyolefin resins preferably comprise a major portion of the resins in the composite (e.g., 60% by weight or more).

Upon melting, the polyolefin resin wets the surfaces of the mica filler in the blends. Through some as yet undefined mechanism it is believed that the wetting and bonding is enhanced when the additives of this invention are included in the blends.

Propylene resins are especially benefited by this invention, particularly those with intrinsic viscosities of above 1.5 and preferably about 2.0–2.6 for processing expedience, although those with higher intrinsic viscosities may also be suitably employed. The propylene resins may comprise propylene homopolymer or propylene copolymer or mixtures thereof, such copolymers normally comprising at least about 75 mole percent propylene and up to 25 mole percent of other monomers such as ethylene and butene-1. The preferred propylene resins comprise propylene homopolymer or copolymer normally made with stereospecific catalysts. Desirably, these propylene resins are in flake or powder form and pass through a 20 mesh screen, more preferably a 60 mesh screen, and, although currently available propylene resins are substantially retained on a 325 mesh screen, even smaller sizes may be used in this invention. Ethylene resins such as polyethylene homopolymer or ethylene copolymers made with aliphatic olefin hydrocarbons as propylene, butene-1 and hexene-1 are also particularly desirable.

Mica fillers are commercially available. These fillers can be generally characterized as being derived from aluminum silicate minerals which can be cleaved into thin sheets. Commercially available fillers which comprise principally muscovite, biotite and/or phlogopite micas (e.g., Suzorite Mica marketed by Marietta Resources International) are preferred with mica fillers comprising principally phlogopite mica being currently more preferred. Mixtures of micas can also be employed.

Although various means of preparing highly delaminated mica flakes are employed in the mineral industry, those not employing wet grinding are preferred. Especially preferred are those dry delamination processes in which ore containing in part the various forms of mica is excavated and crushed into lumps for transportation ease. These lumps are further reduced in size by hammer milling in order to free the boxes (or single crystals of mica) from other mineral impurities.

In such dry processes, the single crystals are typically delaminated between counter rotating drums which exert high shearing forces. The degree of delamination, hence the aspect ratio of the resulting mica flakes, is dependent upon the clearances set between the counter rotating drums. The delaminated flakes are then separated from other mineral impurities by vibration and/or air classification techniques with the purfied mica still further classified according to particle size via conventional screening processes.

When prepared in this manner the mica surfaces are relatively free from large amounts of adsorbed species (such as moisture from water grinding) which may cause interference to the additives described in this invention.

Mica flakes, especially those comprising principally phlogopite mica, having an aspect ratio (mean diameter to thickness measured by the film balance technique) of at least about 30 (more preferably at least about 60 so as to minimize breakage effects during processing) and up to 200 or higher are preferably employed. Mica flakes which are retained on a 100 mesh screen, more preferably on a 60 mesh screen, are normally more desirable, but mica which passes through a 325 mesh can also be employed. Mica flakes which substantially pass through a 20 mesh screen are advantageous for processing expedience.

The additive which strengthens the mica and polyolefin resin adhesion is employed in minor amounts (e.g., 0.05-10%, but preferably between about 0.5-5%) by weight of the combined weight of mica and polyolefin resin, sufficient to strengthen the composite. For example, resinous chlorinated waxes are normally used at less than about 3% by weight of the total weight of mica filler and polyolefin resin. ASTM (D-790) Flexural Properties of Plastics is a convenient measure of the strengthening of the composite. Other evidence of the strengthening may be seen in, for example, enhanced tensile strength, flexural modulus and heat deflection temperature as well as reduction of mold shrinkage.

The chlorinated aliphatic compounds preferred in this invention have a molecular weight (number average) in a range of about 500-10,000 (more preferably about 800-5,000) and a chlorine content of from about 5-80% by weight.

High levels (e.g., about 60-80%) by weight chlorine are desirable for chlorinated saturated hydrocarbons such as chlorinated paraffin waxes. Lower levels (e.g., about 5-50%) of chlorine by weight are especially suitable, if there is additional polarity (e.g., carboxyl groups) or unsaturation in the chlorinated aliphatic compounds. Lower molecular weight e.g. 250 can be used, especially when there is a high level of chlorine by weight.

Examples of additives comprising chlorinated aliphatic compounds include chlorinated hydrocarbons such as resinous chlorinated paraffin waxes (e.g., those marketed as Chlorowax [Diamond Shamrock], Klorochek [Keil Chemical, a division of Ferro Chemical] and Chlorez [Dover Chemical, a division of ICC]). Resinous chlorinated waxes with molecular weights of about 800-1200 are preferred, as, for example, Chlorowax 70.

In one preferred method of making composites of this invention, particulate (powder, flake) polyolefin resin, mica flakes and a powdered additive comprising chlorinated aliphatic compounds are admixed by tumbling (preferably non-intensive) followed by extrusion compounding of the blend with vacuum venting. The extrusion compounder is fitted at the end with a heated pipe which lengthens the time the passing melt is exposed to a high temperature. For propylene resin, mica flakes comprising, for example, phlogopite mica, and resinous chlorinated paraffin waxes, a total time elapsed after melting (i.e., melt residence time) of about 5-10 minutes at about 190°-210° C. is preferred before melt is cooled. Subsequent heating, as by annealing and drying may also be used to contribute to this residence time. The melt can be shaped thereafter by molding but other fabrication techniques can be employed.

In another preferred method of making, the mica itself is first blended with the additive comprising one or more chlorinated aliphatic compounds to preferably provide a coating on the mica particles (e.g. flakes). Resinous chlorinated aliphatic hydrocarbon as, for example, chlorinated paraffin wax is desirably melted (at up to about 15% by weight, more preferably up to about 2% by weight of the weight of mica) onto the mica preferably at high temperature (e.g., 150° C.) but desirably below that temperature which would cause severe decomposition and deterioration of the strengthening effect attributed to the additive. This melt coating is desirably conducted during gentle mixing of the mica particles and the additive to achieve uniformity of the coating and minimize breakage of the particles. Preferably, the mica is dried prior to melt coating with the additive. Advantageously, the melt coating can be accomplished in less than one hour, normally less than 15 minutes depending on such factors as equipment mixing, conditions and temperature. The coating of the mica has the advantage of providing greater uniformity for the blends as compared to mixing the ingredients separately. The coated mica is further compounded preferably by admixture with the polyolefin resin to form a dry powder blend for further processing.

Temperatures between about 170°-300° C. are typically suitable during such preferred above-described compoundings with the polyolefin resin. Higher temperatures with this range, e.g., 220° C. or higher, usually require shorter times for optimum development of properties while lower temperatures require longer periods. Advantageously, the additives of this invention provide stable subsequently produced mechanical properties at usual melt temperatures for long periods, e.g., 30 minutes or longer. Normally it is desirable to allow a period between about one (1) and 30 minutes at melt temperature, more desirably between about 5-15 minutes. Subsequent operations as shaping at melt conditions can contribute to this melt residence time.

After compounding, the melt, preferably having resided for an extended period at melt temperature, can be passed to a cooling zone and thereafter cut (e.g., diced) into particles suitable for shaping processes. Alternatively, the melt may be passed directly into a shaping operation. Shaping, if done by injection molding, is preferably performed at about 3,000-9,000 psi at temperatures of about 190°-210° C. into molds held at about 30°-70° C.

Other shaping operations such as extrusion, compression or blow molding or stamping and the like may be employed. Further, shaping operations can be used to maintain a time and temperature sufficient to strengthen the composite. Moreover, rods, sheets, tubes and films also can be fabricated and receive the benefits of this invention.

It is to be understood that blends of this invention may include combinations of fillers such as mica with glass fibers or mica with talc as well as minor amounts of additives (e.g., stabilizers, pigments, lubricants and the like) which are conventionally included during processing of composites. For example, alkaline earth oxides (e.g. MgO, CaO) may be included at up to about 5% of the composite weight and are advantageous to absorb gases resulting from entrapped moisture or decomposition of the additive generated during high temperature compounding or melt forming processes.

The following examples are intended to illustrate this testing in this first set are made after first purging the molding machine with 10 shots of the individual formulations spaced one minute apart followed by shots taken at intervals spaced by the time as indicated in Table 2.

TABLE 1

FORMULATIONS

| FORMULATION NUMBER | \multicolumn{10}{c|}{Formulations in Part by Weight} | | | | | | | | | |
| --- | --- | --- | --- | --- | --- | --- | --- | --- | --- | --- |
|  | 1 | 2 | 3 | 4 | 5 | 6 | 7 | 8 | 9 | 10 |
| Propylene Resin | | | | | | | | | | |
| Homopolymer (Hercules Pro Fax 6523-PM) | 100.0 | 70.0 | 70.0 | 60.0 | 50.0 | 70.0 | 70.0 | — | — | — |
| Copolymer (Hercules Pro Fax 8523-PM) | — | — | — | — | — | — | — | 70.0 | — | — |
| Polyethylene Resin | | | | | | | | | | |
| (USI Microthene MA-778) | — | — | — | — | — | — | — | — | 60.0 | 60.0 |
| Mica Filler (particle size) | | | | | | | | | | |
| Suzorite "GPA" 1 (passes through 20 mesh but retained on 60 mesh) | — | 30.0 | 30.0 | 40.0 | 50.0 | — | 30.0 | 30.0 | 40.0 | 40.0 |
| Suzorite "-325-5" (passes through 325 mesh) | — | — | — | — | — | 30.0 | — | — | — | — |
| Additive | | | | | | | | | | |
| Chlorowax 70-LP 2 | 1.0 | — | 1.0 | 1.0 | 1.0 | 1.0 | — | 1.0 | — | 1.0 |
| Polyclefin 310-6 3 | — | — | — | — | — | — | 1.0 | — | — | — |

1 - Principally phlogopite mica (Marietta International)
2 - About 70% by weight chlorine (Diamond Shamrock)
3 - About 19% chlorine by weight; viscosity in xylene (50% by weight) 4000 cp at 25° C.; Specific gravity 1.54; and softening point (Vicat) of 105° C.; marketed by Eastman Chemical.

| Formulation Number | Processing Temperature | \multicolumn{10}{c|}{Flexural Yield Strength - psi - ASTM-D790} | | | | | | | | | |
| --- | --- | --- | --- | --- | --- | --- | --- | --- | --- | --- | --- |
|  |  | 1* | 2* | 3* | 4* | 5* | 10* | 15* | 20* | 30* | 60* |
| 1 | 200° C. | 7,589 | 7,469 | 7,264 | 7,159 | 6,772 | 6,356 | — | 6,461 | 6,019 | 5,998 |
| 2 | 200° C. | 7,627 | 7,492 | 7,495 | 7,576 | 7,555 | 7,303 | 7,226 | 7,215 | 7,225 | — |
| 3 | 200° C. | 7,829 | 7,884 | 8,070 | 8,013 | 8,257 | 8,507 | 9,389 | 9,486 | 9,580 | 9,744 |
| 3 | 285° C. | 8,971 | 8,659 | 7,814 | 6,560 | — | — | — | — | — | — |
| 4 | 200° C. | 7,488 | 7,438 | 7,629 | 8,246 | 8,966 | 9,600 | — | 10,166 | 9,735 | 9,519 |
| 5 | 200° C. | 7,952 | 8,523 | 9,596 | 10,275 | 10,832 | 11,131 | — | 11,079 | 10,331 | 10,507 |
| 6 | 200° C. | 8,584 | 8,769 | 9,300 | 9,749 | 9,781 | 10,048 | 10,062 | 9,978 | 10,028 | 10,044 |
| 7 | 200° C. | 9,429 | 8,941 | 9,153 | 8,725 | 8,937 | 8,625 | 8,660 | — | 8,419 | 8,343 |
| 8 | 200° C. | 5,116 | 5,099 | 5,030 | 5,513 | 6,012 | 6,309 | 6,595 | 6,659 | 6,495 | 6,413 |
| 9 | 200° C. | 3,788 | 3,634 | 3,802 | 3,879 | 3,802 | 3,821 | 3,736 | 3,747 | 3,886 | — |
| 10 | 200° C. | 6,071 | 6,171 | 6,250 | 6,261 | 6,331 | 6,193 | 6,082 | 6,029 | 6,177 | — |

*Time between successive shots (minutes)

invention and are not intended as limiting thereof as those skilled in the art will appreciate that many modifications of these examples can be made within the scope of this invention. All parts are parts by weight, all temperatures are in degrees centigrade and all tests are ASTM standards as noted, unless specifically indicated otherwise.

EXAMPLE 1

In this example, composites are formed into standard ASTM specimens from formulations having varying levels and types of polyolefin resin, mica flakes, and chlorinated aliphatic compounds.

The composites are prepared by dry blending (non-intensive mixing) the resin (powder form), mica flakes and additives comprising the chlorinated aliphatic compounds. Thereafter, the powdery mixture is added to a reciprocating screw injection molding machine (Arburg 200U, 42 ton, 2 oz.), held at 200° C. for times indicated by Table 2 and injected into the mold having a temperature of 30° C. Shot size setting is at 6.3.

The formulation of the composites prepared appear in Table 1.

Properties that are obtained from a first set of composites appear in Table 2. The composites for ASTM In Table 3, the effect of the additive is seen by comparison of properties of composites made with and without the additive of this invention. The formulation used in making composites A and B in Table 3, below, corresponds to formulation 4 of Table 1, except that the formulation of B does not include the additive of this invention. Chlorowax ®70-LP is used as the additive in A. The ASTM specimens having properties as set forth in Table 3 are made as those above except that the molding cycle is set for 10 minutes and the first ten specimens are discarded to approximate a steady state condition. Sufficient specimens are thereafter collected to perform the ASTM tests in Table 3.

TABLE 3

PHYSICAL PROPERTIES

| Physical Property | Units | Composite A With Additive | Composite B Without Additive |
| --- | --- | --- | --- |
| TENSILE STRENGTH ASTM-D638 | psi | 5,600 | 4,100 |
| FLEXURAL STRENGTH ASTM-D790 | psi | 10,250 | 7,200 |
| FLEXURAL MODULUS | psi | 1,127,000 | 850,000 |

TABLE 3-continued

PHYSICAL PROPERTIES

| | | Composite | |
|---|---|---|---|
| | | A | B |
| Physical Property | Units | With Additive | Without Additive |
| ASTM-D790 IZOD IMPACT ASTM-D256 | ft-lbs | 1.25 | 1.30 |
| HEAT DEFL. TEMP ASTM-D648 | °F. | | |
| | @66 psi | 301 | 266 |
| | @264 psi | 272 | 210 |
| MOLD SHRINKAGE ASTM-D955 | in/in | | |
| | length | .002 | .010 |
| | width | .010 | .007 |
| | thickness | .020 | .023 |

EXAMPLE 2

In this example, composites are made from formulations containing 30 parts by weight Hercules Pro-Fax 6523-PM propylene resin and 70 parts by weight muscovite mica flakes (K-100 English Mica Co.) with and without 1 part by weight Chlorowax 70-LP powder. The procedure of Example 1 is followed and ASTM specimens are obtained at the time intervals indicated by Table 2.

The composites made with the additive of this invention show an ASTM-D790 Flexural Yield Strength that is higher than composites made without the additive.

EXAMPLE 3

In this example, the formulations 3-8 of Example 1 are modified by the inclusion of 1 additional part by weight of the individual chlorinated aliphatic compounds. Composites are made and tested by a method similar to that described in Example 1 and likewise show the desirable strengths attained by inclusion of the additive of this invention as compared to composites without the additive.

EXAMPLE 4

The formulation of number 4, Table 1 is compounded in an extrusion compounder (2 inch Transfermix, manufactured by Sterling Extruder Corp.) having a heated pipe extension (length 50 inches, inner diameter 2.25 inches) fitted at the end. The compounder is operated so that the passing melt has a residence of about 9 minutes at 200° C. during extrusion and passage through the heated pipe. The melt is cooled and then diced into pellets. The pellets are fed into an injection molder and molded into ASTM specimens. These specimens are tested and show advantageous properties as compared to ones which do not have the additive of this invention and which are made in the same manner.

EXAMPLE 5

The formulation of number 4, Table 1 is modified by the addition of 5 parts by weight of commercial glass fiber (Owens-Corning, Fiberglass 885, ¼ inch chopped strand, aspect ratio of about 500 to 1). Processing is done as in Example 1 above. Higher Yield Strength values (ASTM D-790) are seen in these composites which are molded into ASTM specimens as compared to composites made in the same manner for like periods but without the additives of this invention.

EXAMPLE 6

Two parts by weight of a resinous chlorinated paraffin (Chlorez 700 of Dover Chemical) is combined 98 parts by weight Suzorite GPA mica (Marietta Resources) by gently mixing in a V-shaped blended at room temperature for about 3 minutes. Thereafter, this admixture is heated up to about 150° C. with gentle mixing continued whereupon a coating of the surface of the mica occurs and the brassy color of the mica begins to turn to a dark red gold. Small portions of the mica mixture are taken to see if the coating is complete by seeing if the surface is still wetted with water.

Mica coated in this manner with additive is used in place of the mica and additive of Example 4 and compared with a formulation containing no additive using the conditions of Example 4. Improved properties are seen in composites made in accordance with this invention.

EXAMPLE 7

One part by weight of Chlorowax 70 (Diamond Shamrock) is used to coat 40 parts by weight of mica (Suzorite GPA, Marietta Resources) in two ways. In Sample (A), the mica is preheated to 200° C. for several minutes prior to addition of the Chlorowax at that temperature. In sample (B), the Chlorowax 70 is added at room temperature prior to heating at 200° C. The coated mica samples are each allowed to cool then separately blended with 60 parts of weight of Hercules Profax 6501 PM polypropylene and injected molded at 200° with an extended molding cycle. The following properties are obtained with ASTM testing:

| | A | B |
|---|---|---|
| Flexural Strength | 8500 psi (mean of 5) 280 psi (std. deviation | 7778 (mean of 5) 395 (std. deviation |
| Flexural Modulus | 1,013,346 psi (mean of 5) 61,612 psi (std. deviation) | 1,087,952 (mean of 5) 57,271 (std. deviation) |

As previously mentioned, a preferred compounding technique in accordance with this invention utilizes an extruder that provides extended periods at melt temperatures for development of optimum mechanical properties of the composites. Basically, this may be accomplished if desired, by including a melt holding chamber between the gate and the die (or nozzle) of an extruder or the extruder portion of a more complex (i.e. injection, blow molding, foam, sheet, etc.) system. Inclusion of this melt holding chamber enables desired production rates to be maintained. The actual dimensions, of course, of the chamber will be determined by the relative output rate desired as well as physical space available. In certain specialized instances, however, usual equipment such as large shot size injection molding devices may be used to mold small parts whereby the melt exists for longer than usual times so that optimum properties develop.

What is claimed is:

1. A silane-free composite made by a process which comprises:
   A. providing a blend consisting essentially of melt forming resin made from monomers comprising olefinic hydrocarbon monomers, mica and a strengthening amount of an additive that is a minor amount by weight of the combined weight of the resin and mica, the additive consisting essentially of one or more chlorinated aliphatic compounds having a molecular weight of about 250–10,000 and about 5–80% chlorine by weight;

B. maintaining the silane-free blend of step A as a melt at a temperature in a range between about 170°–300° C. for a time sufficient to strengthen the composite; and C. cooling said silane-free blend to a temperature below the softening point of said composite.

2. A composite made according to claim 1, wherein the resin comprises one or more selected from the group consisting of polyethylene, polypropylene, copolymers comprising ethylene, propylene and mixtures thereof.

3. A composite made according to claim 1, wherein the resin comprises polypropylene.

4. A composite made according to claim 1, wherein the mica comprises biotite, phlogopite or muscovite mica or mixtures thereof.

5. A composite made according to claim 4, wherein the mica comprises phlogopite mica.

6. A composite made according to claim 5, wherein the molecular weight of the chlorinated aliphatic hydrocarbons is in a range of about 800–5,000.

7. A composite made according to claim 5, wherein the additive consists essentially of resinous chlorinated paraffin wax having about 60–80% by weight chlorine.

8. A composite made according to claim 7, wherein the resin comprises one or more selected from the group consisting of polyethylene, polypropylene, copolymers comprising propylene, ethylene and mixtures thereof.

9. A composite made according to claim 8, wherein the resin comprises polypropylene.

10. A composite made according to claim 9, wherein the additive comprises from about 0.2–3% by weight of the combined weight of the mica filler and resin.

11. A composite made according to claim 10, wherein the weight ratio of mica to resin is about 5:2–2:5 and the melt is maintained for at least about five minutes at a temperature of at least about 170° C.

12. A composite made according to claim 1 wherein said mica in (A) has been combined with the additive to provide a coating on at least a portion of the mica particles.

13. A composite according to claim 12, wherein the additive consists essentially of a resinous chlorinated hydrocarbon having between about 60–80% by weight chlorine.

14. A composite according to claim 13, wherein the mica and the resinous chlorinated hydrocarbon having between about 60–80% by weight chlorine are combined by heating at a temperature above the melting temperature of the resinous chlorinated hydrocarbon to provide a coating on at least a portion of the mica particles and the resin comprises polypropylene.

15. A composite according to claim 14, wherein the mica and additive consisting essentially of one or more chlorinated aliphatic compounds are combined at a temperature above the melting temperature of the additive.

16. A silane-free composite made by a process which comprises:

A. providing a blend consisting essentially of melt forming resin made from monomers comprising olefinic hydrocarbon monomers, mica and a strengthening amount of an additive that is a minor amount by weight of the resin and mica, the additive consisting essentially of one or more chlorinated aliphatic compounds having a molecular weight between about 250–10,000 and about 5–80% by weight chlorine and wherein the mica is combined with the additive to provide a coating on at least a portion of the mica particles;

B. maintaining the silane-free blend of step A as a melt at a temperature in a range between about 170°–300° C. for a time sufficient to strengthen the composite; and C. cooling said silane-free blend to a temperature below the softening point of said composite.

17. A composite made according to claim 2, wherein the chlorinated aliphatic hydrocarbons comprise resinous chlorinated paraffin wax having a molecular weight between about 800–5,000 and about 60–80% by weight chlorine.

18. A composite made according to claim 17, wherein the additive comprises up to about 15% by weight of the mica.

19. A composite made according to claim 18, wherein the weight ratio of mica to resin is about 5:2–2:5.

20. A process for making a silane-free composite which comprises:

A. providing a blend consisting essentially of melt forming resin made from monomers comprising olefinic hydrocarbon monomers, mica and a strengthening amount of an additive that is a minor amount by weight of the resin and mica, the additive consisting essentially of one or more chlorinated aliphatic compounds having a molecular weight between about 250–10,000 and about 5–80% by weight chlorine and wherein the mica is combined with the additive to provide a coating on at least a portion of the mica particles;

B. maintaining the silane-free blend of step A as a melt at a temperature in a range between about 170°–300° C. for a time sufficient to strengthen the composite; and C. cooling said silane-free blend to a temperature below the softening point of said composite.

21. A process according to claim 20, wherein the resin comprises one or more selected from the group consisting of polyethylene, polypropylene, copolymers comprising ethylene, propylene and mixtures thereof.

22. A process according to claim 20, wherein the resin comprises polypropylene.

23. A process according to claim 20, wherein the mica filler comprises biotite, phlogopite or muscovite micas or mixtures thereof.

24. A process according to claim 23, wherein the mica comprises phlogopite mica.

25. A process according to claim 24, wherein the molecular weight of the chlorinated aliphatic hydrocarbons is in a range of about 800–5,000.

26. A process according to claim 24, wherein the additive consists essentially of resinous chlorinated paraffin wax having about 60–80% by weight.

27. A process according to claim 26, wherein the resin comprises one or more selected from the group consisting of polyethylene, polypropylene, copolymers comprising propylene, ethylene and mixtures thereof.

28. A process according to claim 27; wherein the resin comprises polypropylene.

29. A process according to claim 28, wherein the additive comprises from about 0.2–3% by weight of the combined weight of the mica and resin.

30. A process according to claim 29, wherein the weight ratio of mica to resin is about 5:2-2:5 and the melt is maintained for at least about five minutes at a temperature of at least about 170° C.

31. A process according to claim 20, which comprises conjoining the resin with particulate mica that has been combined with the additive to provide a coating on at least a portion of the mica particles.

32. A process according to claim 31, wherein the additive consists essentially of a resinous chlorinated hydrocarbon having between about 60-80% by weight chlorine.

33. A process according to claim 32, wherein the mica and the resinous chlorinated hydrocarbon having between about 60-80% by weight chlorine are combined by heating at a temperature above the melting temperature of the resinous chlorinated hydrocarbon to provide a coating on at least a portion of the mica particles and the resin comprises polypropylene.

34. A process according to claim 33, wherein the mica and additive consisting essentially of one or more chlorinated aliphatic compounds are combined at a temperature above the melting temperature of the additive.

35. A process for making a silane-free composite, which comprises:

A. providing a blend consisting essentially of melt forming resin made from monomers comprising olefinic hydrocarbon monomers, mica and a strengthening amount of an additive that is a minor amount by weight of the resin and mica, the additive consisting essentially of one or more chlorinated aliphatic compounds having a molecular weight between about 250-10,000 and about 5-80% by weight chlorine and wherein the mica is combined with the additive to provide a coating on at least a portion of the mica particles;

B. maintaining the silane-free blend of step A as a melt at a temperature in a range between about 170°-300° C. for a time sufficient to strengthen the composite; and C. cooling said silane-free blend to a temperature below the softening point of said composite.

36. A process according to claim 35, wherein the chlorinated aliphatic hydrocarbons comprise resinous chlorinated paraffin wax having a molecular weight between about 800-5,000 and about 60-80% by weight chlorine.

37. A process according to claim 36, wherein the additive comprises up to about 15% by weight of the mica.

38. A process according to claim 37, wherein the weight ratio of mica to resin is about 5:2-2:5.

* * * * *